(12) United States Patent
Elahi

(10) Patent No.: US 9,370,415 B2
(45) Date of Patent: Jun. 21, 2016

(54) EXPANDABLE SURGICAL IMPLANT DEVICE

(71) Applicant: Ebrahim Elahi, New York, NY (US)

(72) Inventor: Ebrahim Elahi, New York, NY (US)

( * ) Notice: Subject to any disclaimer, the term of this patent is extended or adjusted under 35 U.S.C. 154(b) by 159 days.

(21) Appl. No.: 13/959,538

(22) Filed: Aug. 5, 2013

(65) Prior Publication Data

US 2015/0039085 A1    Feb. 5, 2015

(51) Int. Cl.
| | | |
|---|---|---|
| *A61F 2/14* | (2006.01) | |
| *A61F 2/00* | (2006.01) | |
| *A61F 9/00* | (2006.01) | |
| *A61F 2/28* | (2006.01) | |

(52) U.S. Cl.
CPC ............. *A61F 2/14* (2013.01); *A61F 2/0059* (2013.01); *A61F 2/2846* (2013.01); *A61F 9/0017* (2013.01); *A61F 2002/2878* (2013.01)

(58) Field of Classification Search
CPC ............. A61B 17/56; A61B 17/8023; A61B 17/0057; A61B 2017/00588; A61B 2017/0061; A61B 2017/00619; A61F 2/14; A61F 2250/0006; A61F 2002/2878; A61F 2/0059; A61F 2/284; A61F 9/00176
See application file for complete search history.

(56) References Cited

U.S. PATENT DOCUMENTS

2006/0116682 A1 * 6/2006 Longo .............................. 606/69
2010/0292801 A1 * 11/2010 Hansell et al. ............. 623/17.16

* cited by examiner

Primary Examiner — Howie Matthews

(57) ABSTRACT

A surgical implant device may include a first substantially planar portion having a first surface area, a second substantially planar portion having a second surface area, and a coupling device for connecting the first substantially planar portion to the second substantially planar portion. The coupling device facilitates expanding and contracting the first and the second substantially planar portion in order to provide an implant surface area corresponding to the first surface area during insertion of the surgical implant within an incision, and having a third surface area corresponding to both the first surface area and at least a portion of the second surface area following insertion of the surgical implant within the incision.

5 Claims, 8 Drawing Sheets

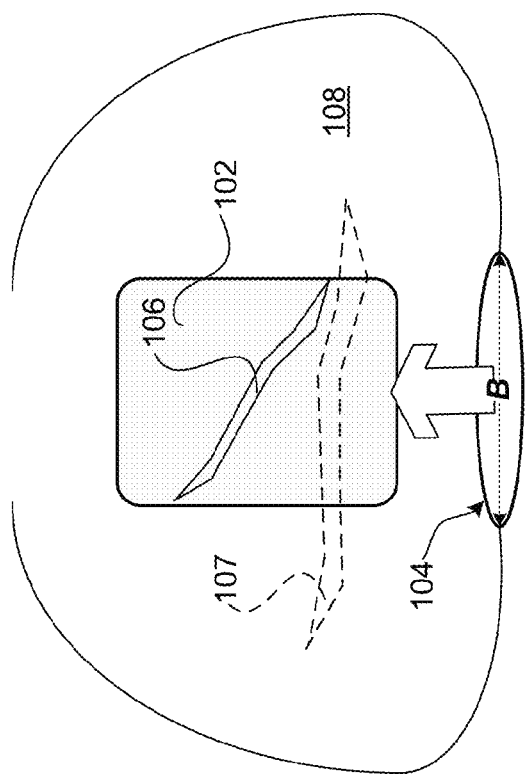
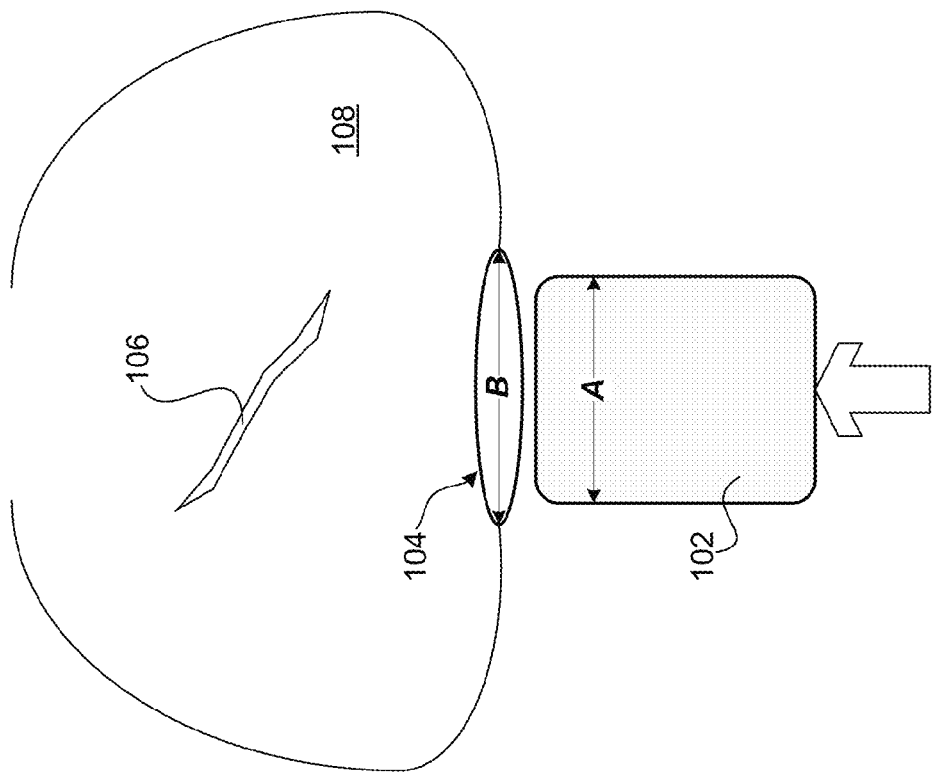
FIG. 1B
FIG. 1A

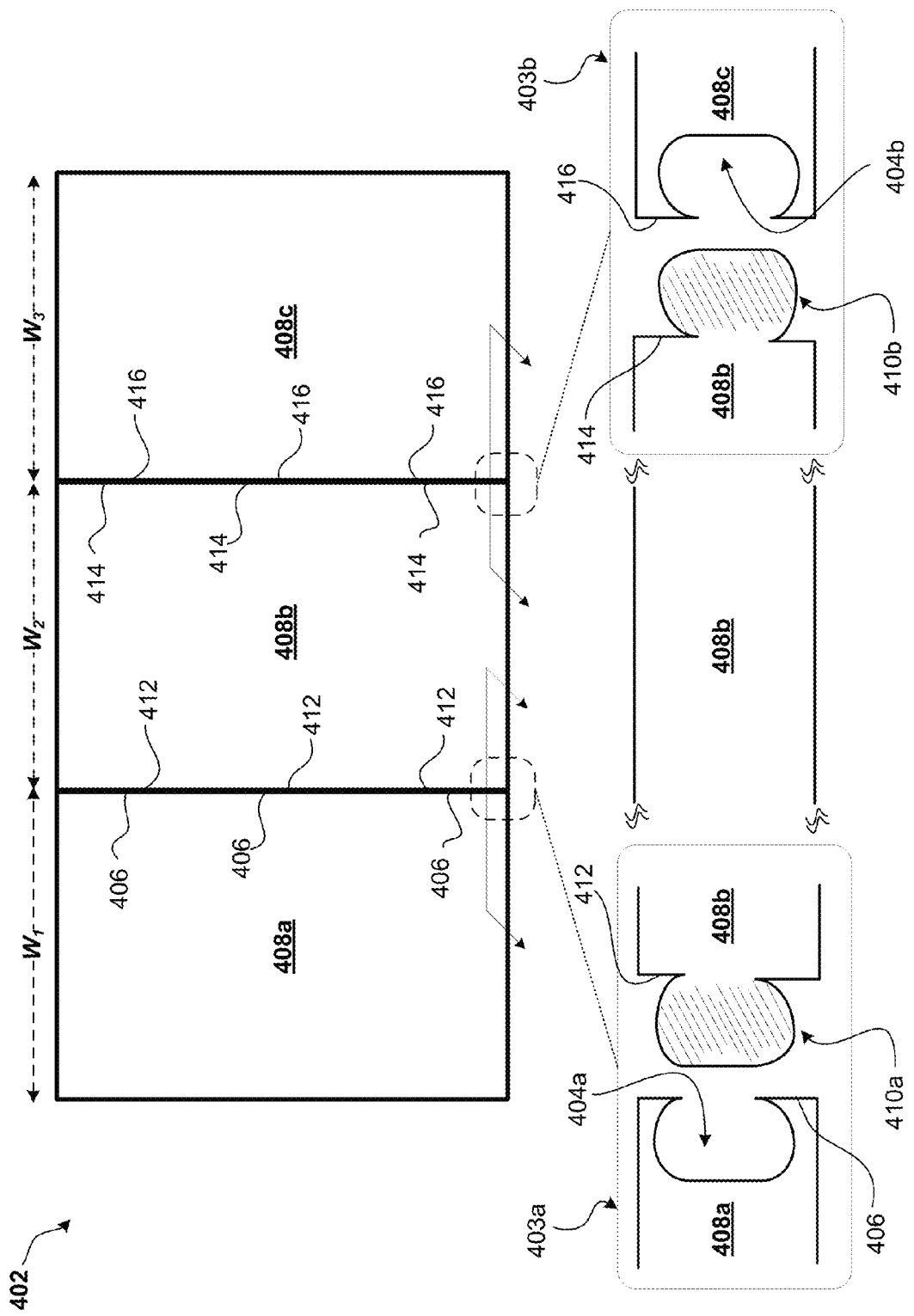

EXPANDABLE SURGICAL IMPLANT DEVICE

BACKGROUND a. Field of the Invention

The present invention generally relates to medical devices, and particularly to surgical implants.

b. Background of Invention

A vast number of surgical procedures require the application of one or more surgical incisions on the patient's body in order allow the medical specialist (e.g., surgeon) to access an area-of-interest. Moreover, in many instances, implant devices may be used to repair or replace an existing component of the body.

For example, in the field of ophthalmology, fracture and damage to the floor or wall(s) of the eye socket (i.e., orbit) as a result of trauma may necessitate the placement of an implant device over the fractured and damaged area.

However, it may be appreciated that generally, the length of the incision used to insert an implant may be proportional to the greatest physical dimension of the implant device needed to address the medical issue. For example, if an applied incision is too small, a requisite implant may not fit through such an incision.

It may, therefore, be advantageous to, among other things, provide implant devices that facilitate smaller incisions, and consequently less surgical trauma, less chance for complications, and faster recovery.

BRIEF SUMMARY

According to at least one exemplary embodiment, a surgical implant device may include a first substantially planar portion having a first surface area, a second substantially planar portion having a second surface area, and a coupling device for connecting the first substantially planar portion to the second substantially planar portion. The coupling device facilitates expanding and contracting the first and the second substantially planar portion to provide an implant surface area corresponding to the first surface area during insertion of the surgical implant within an incision, and having a third surface area corresponding to both the first surface area and at least a portion of the second surface area following insertion of the surgical implant within the incision.

According to another exemplary embodiment, a method of implanting a surgical implant device having an expandable surface area may include making an incision of a first width for implanting the surgical implant device and adjusting the expandable surface area of the surgical implant device to a reduced surface area such that the reduced surface area causes the surgical implant to have a second width that is less than, or substantially the same as, the first width. The surgical implant device having the reduced surface area is placed into the incision. The expandable surface area of the surgical implant device is then adjusted to an increased surface area following the placement of the surgical implant device, such that the reduced surface area causes the surgical implant to have a third width greater than the second width.

According to yet another exemplary embodiment, a method of implanting a surgical implant device may include making an incision of a first width for implanting the surgical implant device. A first substantially planar component associated with the surgical implant device may then be placed into the incision, whereby the first substantially planar component includes a second width that is less than or substantially the same as the first width. Similarly, a second substantially planar component associated with the surgical implant device may be placed into the incision, whereby the second substantially planar component includes a third width that is less than or substantially the same as the first width. The first substantially planar component is coupled to the second substantially planar component, whereby the first substantially planar component includes a first surface area and the second substantially planar component includes a second surface area. The coupling accordingly provides a surface area corresponding to the sum of the first and the second surface areas.

BRIEF DESCRIPTION OF THE SEVERAL VIEWS OF THE DRAWINGS

FIG. 1A illustrates a surgical implant device according to an exemplary embodiment;

FIG. 1B illustrates the insertion of the surgical implant device of FIG. 1A according to an exemplary embodiment;

FIG. 4A depicts an expandable surgical implant device according to yet another exemplary embodiment;

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

According to the following described embodiments, expandable implant devices may be used in order to reduce surgical incision size (e.g., width) for the placement of implants within the body.

Referring to FIG. 1A, a surgical implant device 102 according to an exemplary embodiment is depicted. The surgical implant device 102 is inserted into an incision 104 created by a medical professional (e.g., surgeon), whereby the width, as defined by A, of the surgical implant device 102 may be substantially the same as the width, as defined by B, of the created incision 104. In some implementations, for example, the width A of the surgical implant device 102 may be less than the width B of the created incision 104.

Referring to FIG. 1B, the inserted surgical implant device 102 may be utilized to cover or support an injury, as depicted by 106. According to one non-limiting example, the injury 106 may include a fracture in the floor 108 of an orbital implant. As illustrated, the geometric size of the surgical implant device 102 is selected to be in proportion to the area or size of the injury 106. Thus, the surgical implant device 102 may completely cover the injury 106 (i.e., fracture) in the orbital floor 108. Consequently, the incision width B is created to accordingly facilitate the insertion of the surgical implant device 102. Thus, the larger the surgical implant device 102 is, the larger the corresponding incision 104 needs to be. However, as depicted and described in the following paragraphs, a surgical implant device may be expanded to cover a larger injury.

Figure 2B:
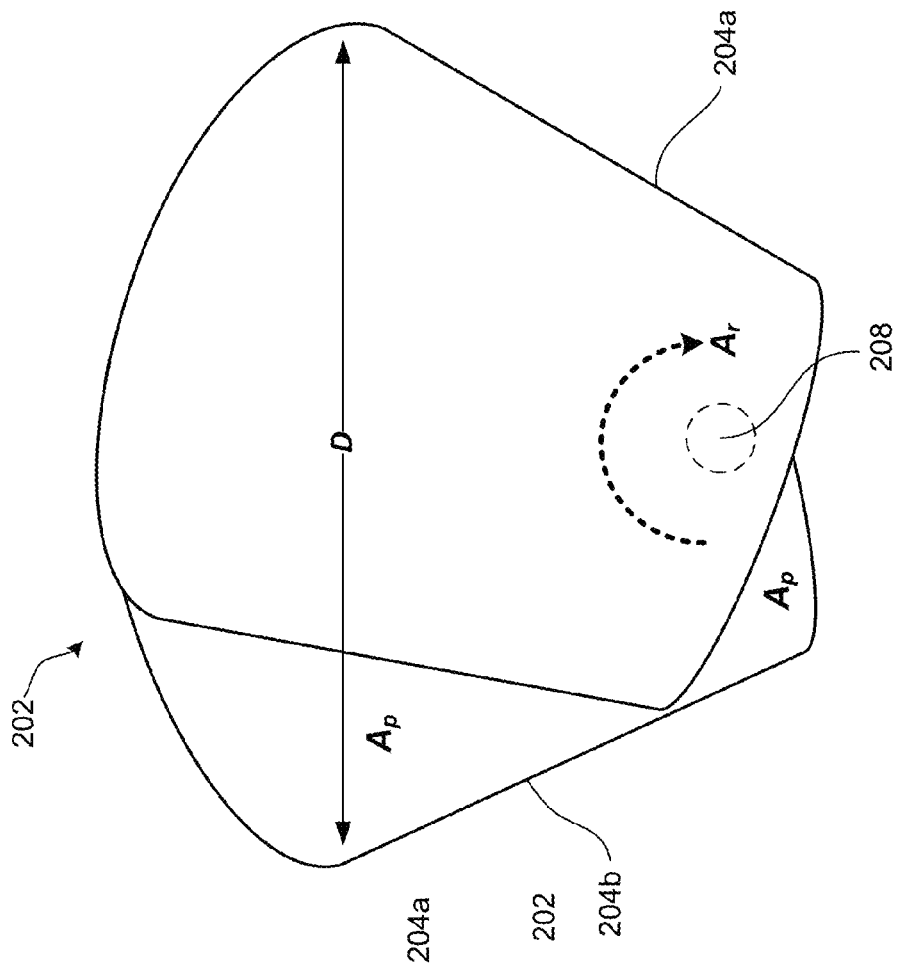
FIG. 2B depicts the expandable surgical implant device of FIG. 2A in an expanded state.
Figure 2A:
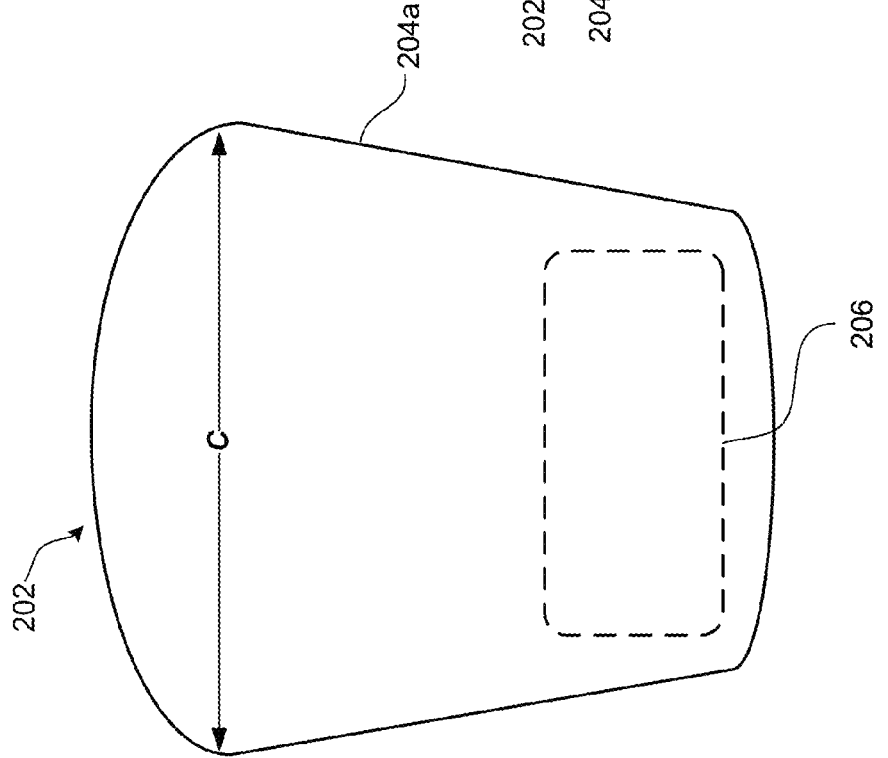
FIG. 2A depicts an expandable surgical implant device in an unexpanded state according to one exemplary embodiment.

Referring to FIG. 2A, one embodiment of an expandable surgical implant device 202 is depicted. In an unexpanded state, surgical implant device 202 may include a width, as defined by C. Thus, surgical implant device 202 may be inserted into, for example, incision 104 (FIG. 1A) based on the width C of the surgical implant device 202 being substantially the same as or smaller than the width B of the incision 104 (FIG. 1A). Referring to FIG. 2B, however, in an expanded state, surgical implant device 202 may be manipulated to a larger width area, as defined by D, once the surgical implant device 202 is placed within the incision 104 (FIG. 1B).

For example, if an injury 107 (FIG. 1B) is more extensive and, thus, extends over a greater area of the orbital floor or wall 108 (FIG. 1B) compared to injury 106 (FIG. 1B), the surgical implant device 202 may be expanded to width D in order to have a larger surface area compared to when the surgical implant device 202 has a smaller surface area in the unexpanded state (i.e., at width C). The larger surface area of the surgical implant device 202 may now facilitate covering the more extensive injury 107 (FIG. 1B) without the disadvantage associated with the requisite need for creating a larger incision relative to incision 104 (FIG. 1B). Thus, a smaller incision width (e.g., FIG. 1B: width B) may be created for larger injuries (e.g., FIG. 1B: incision 107) by inserting a surgical implant device in an unexpanded state (e.g., FIG. 2A: device 202) having a smaller width (e.g., FIG. 2A: width C), and subsequently expanding the surface area and width (e.g., FIG. 2B: width D) of the surgical implant device (e.g., FIG. 2B: device 202) to cover the larger injury once the device has been inserted.

As depicted in FIG. 2A, in the unexpanded state, the surgical implant device 202 may include two substantially planar surfaces that almost entirely overlap. As shown, the top planar surface 204a and the bottom planar surface 204b are completely overlapping such that only top planar surface 204a is visible in FIG. 2A. Referring to FIG. 2B, the top planar surface 204a and the bottom planar surface 204b may be rotatably manipulated, as indicated by arrow $A_r$, such that the top planar surface 204a and the bottom planar surface 204b fan-out to partially overlap. Therefore, as illustrated, the total surface area of the manipulated surgical implant device 202 increases to the sum of the surface area of the top planar surface 204a and at least a portion $A_p$ of the surface area of the bottom planar surface 204b.

Referring to FIG. 2A, region 206 of the surgical implant device 202 may, for example, include a coupling device (e.g., see FIG. 2C) that both provides a rotatable coupling and positional retention capability between the top planar surface 204a and the bottom planar surface 204b. Referring to FIG. 2B, a swiveling mechanism 208 may rotatably couple the top planar surface 204a and the bottom planar surface 204b of the surgical implant device 202. The following paragraphs provide non-limiting examples of various coupling devices that facilitate the expansion and contraction of implant devices for the purposes of mitigating the need for increased incision sizes that correspond to the area/size of the injury.

Figure 2C:
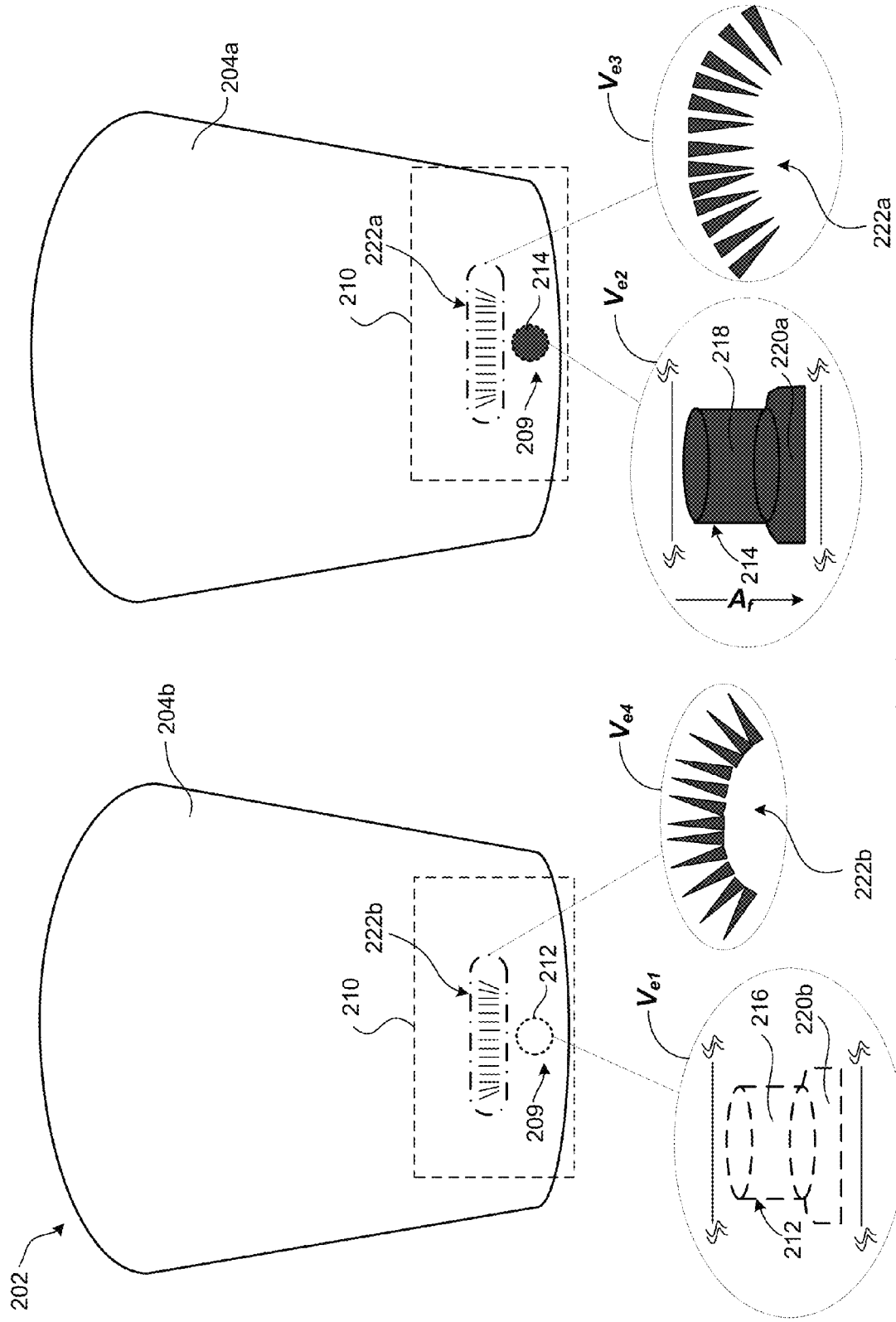
FIG. 2C depicts an exemplary embodiment of a coupling device for providing rotatable coupling and positional retention between top and bottom planar surfaces of the expandable surgical implant device of FIG. 2A.
Figure 2E:
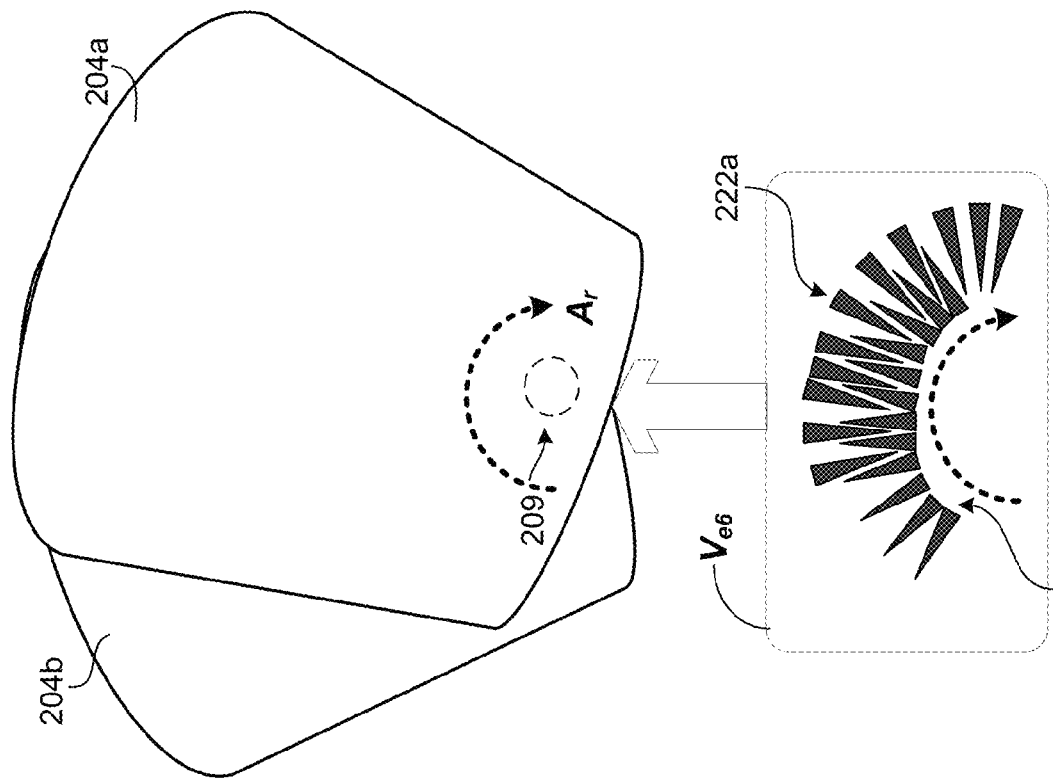
FIG. 2E depicts the interlocking of the top and bottom planar surface of the surgical implant device of FIG. 2A in an expanded state using the interlocking fins according to one exemplary embodiment.

Referring to FIG. 2C, an embodiment of a coupling device 210 for providing rotatable coupling and positional retention between top planar surface 204a and bottom planar surface 204b is depicted. The coupling device 210 may include a swiveling mechanism 209 having a snap fit receptacle 212 located on the bottom planar surface 204b and a snap fit connector 214 located on the top planar surface 204a. As illustrated, the expanded view $V_{e1}$ of snap fit receptacle 212 shows a cylindrical opening 216 that is adapted to receive a connector, whereby the connector has the ability to swivel or rotate within the opening 216. The expanded view $V_{e2}$ of snap fit connector 214 shows a cylindrical plug 218 that is adapted to receive a connector, whereby the connector has the ability to swivel or rotate within the opening 216.

The snap fit receptacle 212 also includes coupling region 220b while snap fit connector 214 also includes coupling region 220a. In operation, the snap fit connector 214 is pushed into snap fit receptacle 212 in the direction of arrow $A_f$. Thus, the coupling region 220a of snap fit receptacle 212 may be forcibly pushed into the cylindrical opening 216 of snap fit receptacle 212 such that coupling region 220a elastically deforms to accommodate the smaller cross-section of the cylindrical opening 216. As coupling region 220a fills coupling region 220b of the snap fit receptacle 212, coupling region 220a elastically expands back to its original non-deformed state. Since the coupling regions 220a, 220b are now mated and have a larger cross-section than the cylindrical opening 216, the snap fit receptacle 212 and the snap fit connector 214 remain coupled together. Thus, the top planar surface 204a and the bottom planar surface 204b are coupled together and may accordingly rotate about the mated snap fit receptacle 212 and connector 214.

The volume and shape of the snap fit connector 214 is substantially the same as, or slightly less than, that of the snap fit receptacle 212 and, therefore, the snap fit connector 214 has the ability to rotate or swivel within the snap fit receptacle 212. The snap fit connector 214 may include a flexible polyethylene material that enables it to deform when forcibly inserted into the snap fit receptacle 212. Moreover, the top planar surface 204a and the bottom planar surface 204b may include a thickness of about 0.6-1.5 millimeters and each may have an embedded titanium mesh.

In order to maintain the top planar surface 204a and the bottom planar surface 204b in a set position after rotation, an interlocking mechanism including a plurality of interlocking fins 222a, 222b corresponding to the top and the bottom planar surfaces 204a, 204b may be utilized. As depicted in expanded view $V_{e3}$, the interlocking fins 222a of the top planar surface 204a may have a substantially downward orientation. Particularly, the substantially downward orientation of the interlocking fins 222a is relative to the plane of surface 204a. Also, as shown in expanded view $V_{e4}$, the interlocking fins 222b of the bottom planar surface 204b may include a substantially upward orientation. Particularly, the substantially upward orientation of the interlocking fins 222b is accordingly relative to the plane of surface 204b.

Figure 2D:
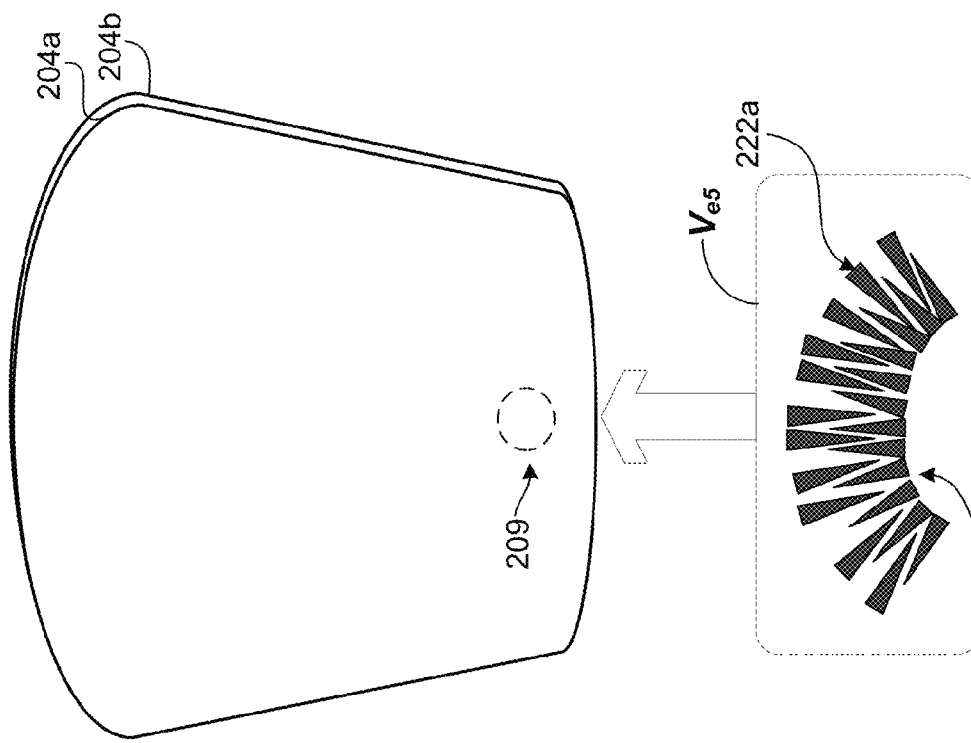
FIG. 2D depicts the interlocking of the top and bottom planar surface of the surgical implant device of FIG. 2A in an unexpanded state using interlocking fins according to one exemplary embodiment.

Referring to FIG. 2D, while the top planar surface 204a and the bottom planar surface 204b of the surgical implant device 202 are in a substantially unexpanded state, as depicted in expanded view $V_{e5}$, the fins of interlocking fins 222a and 222b overlap almost entirely and interlock. Referring to FIG. 2C, as the top and bottom planar surfaces 204a, 204b of the surgical implant device 202 are forcibly manipulated (i.e., along arrow $A_r$) into an expanded state using the swiveling mechanism 209, as depicted in expanded view $V_{e6}$, the top planar surface 204a interlocking fins 222a are repositioned relative to the bottom planar surface 204b interlocking fins 222b.

Although the fins are flexible enough to allow for such repositioning, absent a sufficient external force, the engaged interlocking fins 222a, 222b remain partially overlapping and maintain the expanded position of the top and bottom planar surfaces 204a, 204b of the surgical implant device 202. This may be required since, for example, once the surgical implant device 202 is placed within a patient's incision, the bodily movements of the patient can cause the surgical implant device 202 to contract or collapse from its expanded state. Thus, the interlocking mechanism including the plurality of interlocking fins 222a, 222b avoids such a collapse or contraction of the surgical implant device 202. However, following a finite duration after placement of the surgical implant device 202, the top and bottom expanded planar surfaces 204a, 204b become less susceptible to inadvertent repositioning due to external forces. This may be due to the bio-integration of the surgical implant device 202 within the patient's body and the healing processes corresponding to the surrounding tissue associated with the surgical implant device 202.

In addition, for an orbital implant example, the top and the bottom expanded planar surfaces 204a, 204b may include relative coarse outer surfaces, whereby the coarseness of the outer surfaces enhance the contact stability of the surgical implant device 202 with the orbital floor under the periosteum. Also, in the orbital implant example, the top and bottom expanded planar surface 204a, 204b may include relative smooth outer surfaces, whereby the smoothness of the outer surfaces in contact with the periosteum avoids and/or mitigates any movement inhibitions with the respect to the eyeball located over the surgical implant device 202.

Figure 3A:
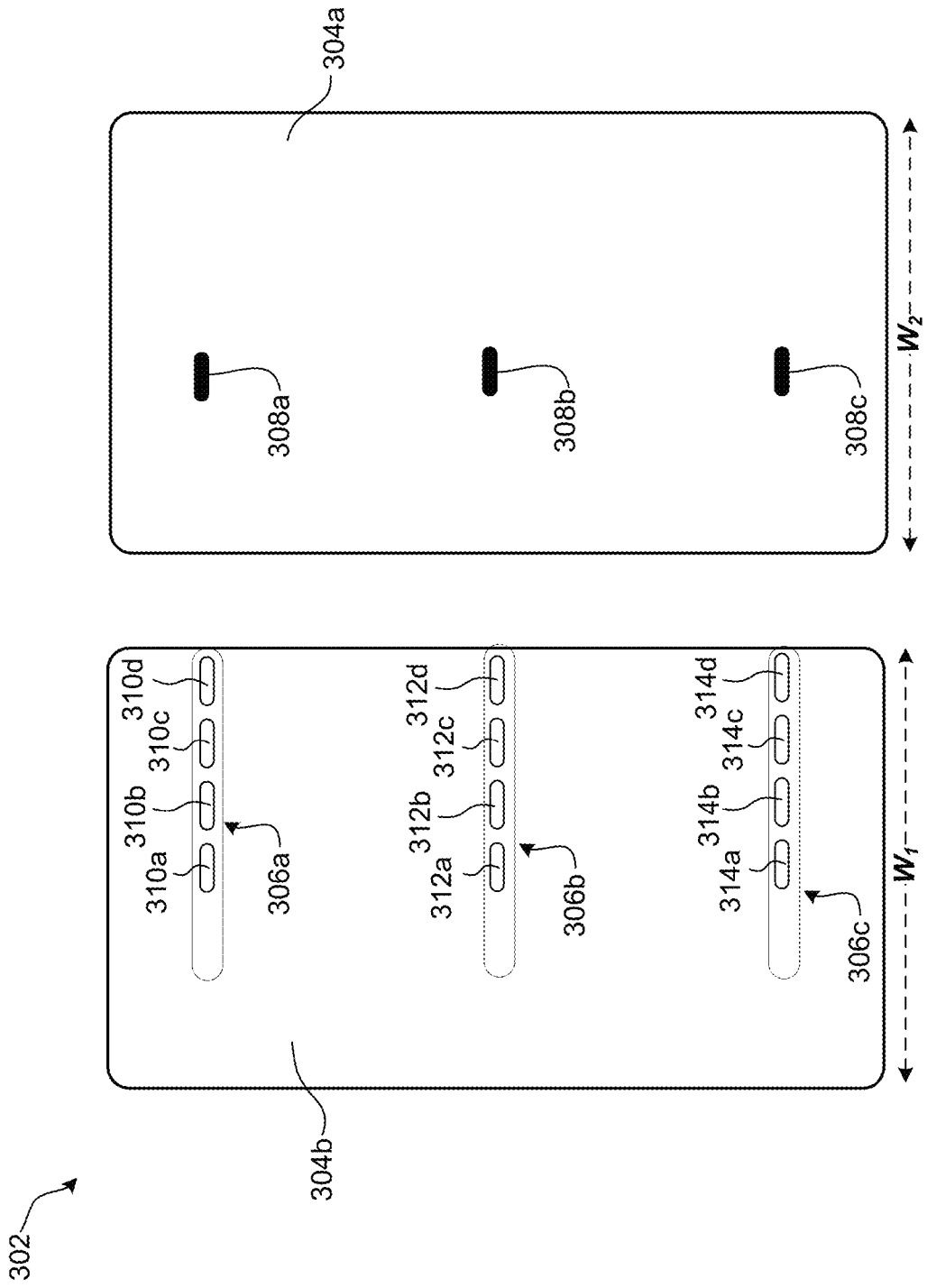
FIG. 3A depicts an expandable surgical implant device according to another exemplary embodiment.

Referring to FIG. 3A, another exemplary embodiment of an expandable surgical implant device 302 is depicted. The expandable surgical implant device 302 may include a top planar surface 304a and a bottom planar surface 304b. The bottom planar surface 304b may include a plurality of snap fit receptacles 306a-306c, while the top planar surface 304a may accordingly include a plurality of corresponding snap fit connectors 308a-308c for engaging any one of the openings within snap fit receptacles 306a-306c. As illustrated, each of the plurality of snap fit receptacles 306a-306c may include several openings. For example, snap fit receptacle 306a includes openings 310a-310d and snap fit receptacle 306b includes openings 312a-312d. Similarly, snap fit receptacle 306c includes openings 314a-314d. In operation, the snap fit connector 308a of top planar surface 304a may couple to any one of the openings 310a-310d within snap fit receptacle 306a. Snap fit connector 308b of top planar surface 304a may couple to any one of the openings 312a-312d within snap fit receptacle 306b. Also, snap fit connector 308c of top planar surface 304a may couple to any one of the openings 314a-314d within snap fit receptacle 306c.

By providing the ability to couple the top planar surface 304a and the bottom planar surface 304b in the described manner, each planar surface may be individually inserted into an incision of substantially the same width as either planar surface, and subsequently coupled together within the region of the body receiving the expandable surgical implant device 302. For example, the bottom planar surface 304b having a width of $W_1$ may be inserted into incision 104 (FIG. 1B) having a width B, whereby the width of $W_1$ of the bottom planar surface 304b may be substantially the same as or smaller than that of the incision 104 (FIG. 1B) width B. Similarly, for example, the top planar surface 304a having a width of $W_2$ may subsequently be inserted into incision 104 (FIG. 1B) having a width B, whereby the width of $W_2$ of the top planar surface 304a may also be substantially the same as or smaller than that of the incision 104 (FIG. 1B) width B. If the incision provides, for example, access to the orbital floor 108 (FIG. 1B) of a patient, then the subsequently inserted top planar surface 304a may be coupled to the already inserted bottom planar surface 304b within the exposed orbital floor 108 region.

For providing a maximum expansion of the area corresponding to expandable surgical implant device 302, the plurality of snap fit connectors 308a-308c of the top planar surface 304a may be coupled (e.g., snap fitted) to openings 310d-314d of the bottom planar surface 304b, respectively. For example, for an intermediate expansion of the area corresponding to expandable surgical implant device 302, the plurality of snap fit connectors 308a-308c of the top planar surface 304a may be coupled (e.g., snap fitted) to either openings 310c-314c or 310b-314b of the bottom planar surface 304b, respectively. A minimum expansion of the area corresponding to expandable surgical implant device 302 may be provided, whereby the plurality of snap fit connectors 308a-308c of the top planar surface 304a may alternatively be coupled (e.g., snap fitted) to openings 310a-314a of the bottom planar surface 304b, respectively.

The snap fit connectors 308a-308c may include a flexible polyethylene material that enables it to deform when forcibly inserted into the respective openings of the snap fit receptacles 306a-306c. Moreover, the top planar surface 304a and the bottom planar surface 304b may also include a thickness in the region of about 0.6-1.5 millimeters and each may have an embedded titanium mesh (not shown).

Figure 3C:
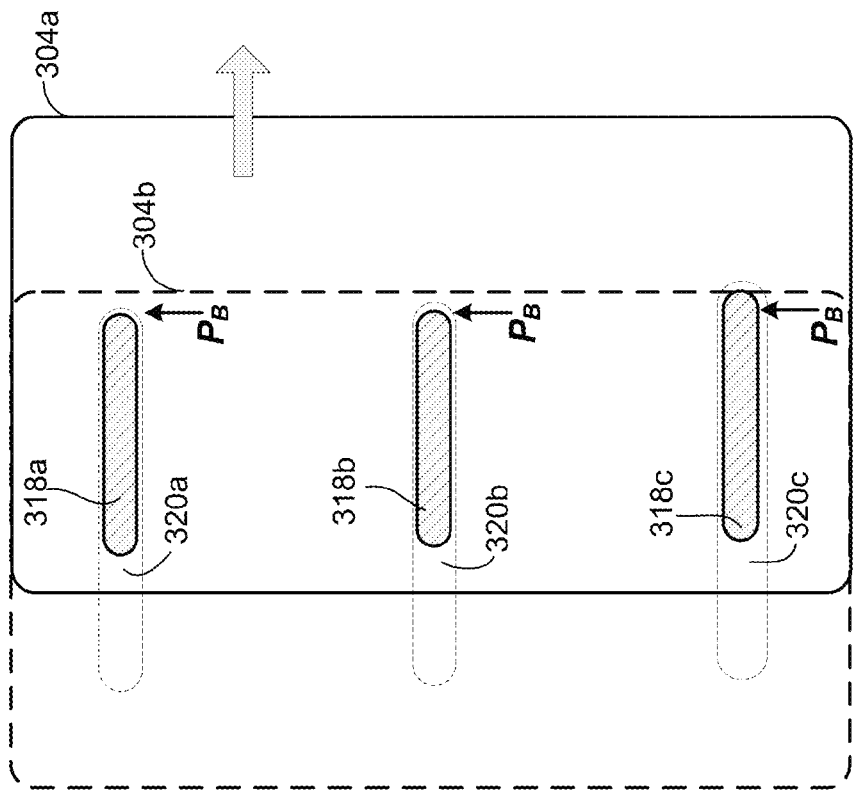
FIG. 3C depicts the modified exemplary embodiment of the expandable surgical implant device of FIG. 3A in a substantially expanded state.
Figure 3B:
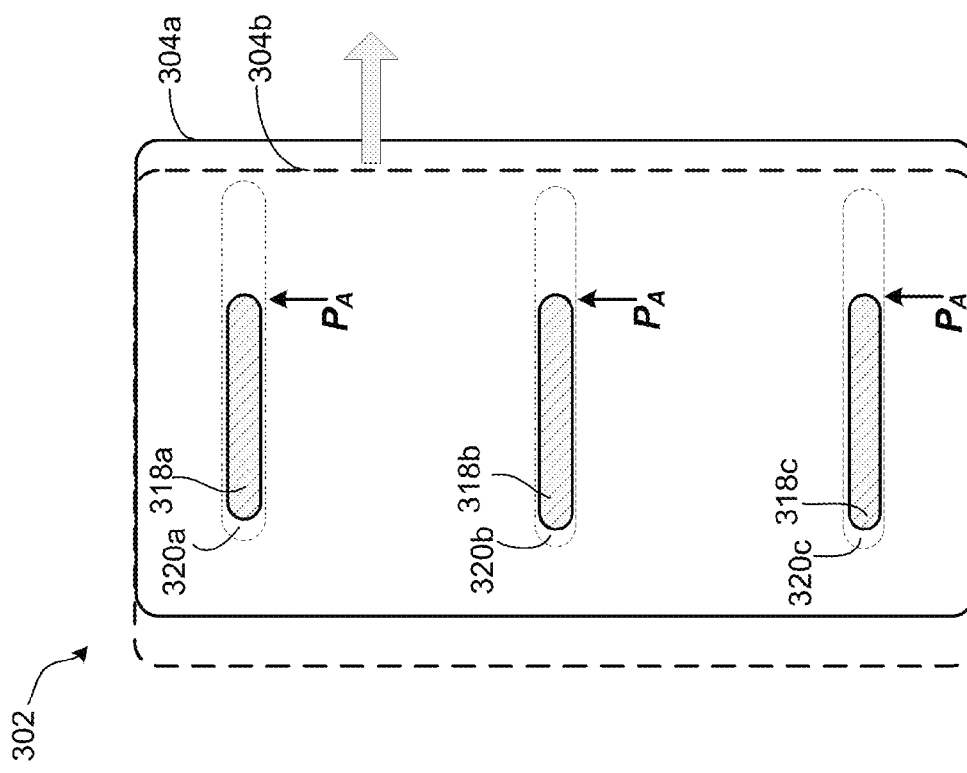
FIG. 3B depicts a modified exemplary embodiment of the expandable surgical implant device of FIG. 3A in a substantially unexpanded state.

Referring to FIG. 3B, a modified exemplary embodiment of the expandable surgical implant device 302 is depicted. As illustrated, the top planar surface 304a may include a top elongate raised portion 318a, while the bottom planar surface 304b may include a corresponding top channel region 320a that receives the elongate raised portion 318a. The top planar surface 304a may also include a center elongate raised portion 318b, while the bottom planar surface 304b includes corresponding center channel region 320b that receives the elongate raised portion 318b. Finally, the top planar surface 304a may include a bottom elongate raised portion 318c, while the bottom planar surface 304b may include corresponding bottom channel region 320c for receiving elongate raised portion 318c.

In operation, the elongate raised portions 318a-318c may snap fit into and slidably move within their respective channel regions 320a-320c. The frictional forces between the coupled elongate raised portions 318a-318c and their respective channel regions 320a-320c may facilitate maintaining a positional relationship between both the top planar surface 304a and the bottom planar surface 304b. For example, referring to FIG. 3C, the combined expanded surface area of the expandable surgical implant device 302, as governed by the non-overlapping portions of the top planar surface 304a and the bottom planar surface 304b, may be increased by sliding elongate raised portions 318a-318c within their respective channel regions 320a-320c from position $P_A$ (FIG. 3B) to position $P_B$. Thus, the frictional forces between the coupled elongate raised portions 318a-318c and their respective channel regions 320a-320c may facilitate maintaining positional relationship $P_B$ between both the top planar surface 304a and the bottom planar surface 304b.

Figure 4C:
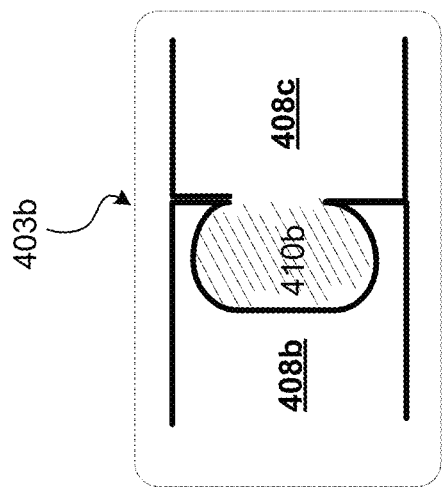
FIG. 4C depicts a second mating receptacle and mating connector for the expandable surgical implant device of FIG. 4A.
Figure 4B:
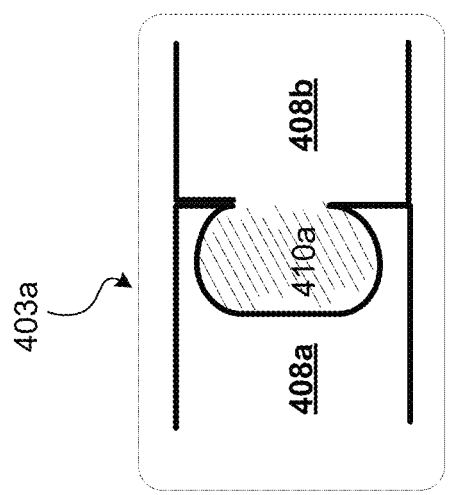
FIG. 4B depicts a first mating receptacle and mating connector for the expandable surgical implant device of FIG. 4A.

Referring to the plan view of FIG. 4A, another exemplary embodiment of an expandable surgical implant device 402 is depicted. As shown in expanded cross sectional view 403a, the surgical implant device 402 may include a mating receptacle 404a located on a vertical edge 406 of a first substantially planar portion 408a. Also, surgical implant device 402 may include a mating connector 410a located on a vertical edge 412 of a second substantially planar portion 408b. The mating connector 410a may snapably interlock with mating receptacle 404a, thereby coupling the first and the second substantially planar portions 408a, 408b (FIG. 4B) at their respective vertical edges 406, 412.

Similarly, additional planar portions may be added to increase the surface area of the expandable implant device 402. Thus, as shown in expanded cross sectional view 403b, the surgical implant device 402 may include a mating receptacle 404b located on a vertical edge 416 of a third substantially planar portion 408c. Also, surgical implant device 402 may include a mating another mating connector 410b located on the other vertical edge 414 of the second substantially planar portion 408b. The mating connector 410b may snapably interlock with mating receptacle 404b, thereby coupling the second and the third substantially planar portions 408b, 408c (FIG. 4C) at their respective vertical edges 414, 416.

By providing the ability to couple the first substantially planar portion 408a, the second substantially planar portion 408b, and the third substantially planar portion 408c in the described manner, each planar portion may be individually inserted into an incision of substantially the same width as either planar region, and subsequently coupled together within the region of the body receiving the expandable surgical implant device 402. For example, the first substantially planar portion 408a having a width of $W_1$ may be inserted into incision 104 (FIG. 1B) having a width B, whereby the width of $W_1$ of the first substantially planar portion 408a may be substantially the same as or smaller than that of the incision 104 (FIG. 1B) width B. Similarly, for example, the second substantially planar portion 408b having a width of $W_2$ may subsequently be inserted into incision 104 (FIG. 1B) having a width B, whereby the width of $W_2$ of the second substantially planar portion 408b may also be substantially the same as or smaller than that of the incision 104 (FIG. 1B) width B. Also, for example, the third substantially planar portion 408c having a width of $W_3$ may subsequently be inserted into incision 104 (FIG. 1B) having a width B, whereby the width of $W_3$ of the third substantially planar portion 408c may also be substantially the same as or smaller than that of the incision 104 (FIG. 1B) width B. If the incision provides, for example, access to the orbital floor 108 (FIG. 1B) of a patient, then the subsequently inserted second and third substantially planar portions 408b, 408c may be coupled to the already inserted first substantially planar portion 408c within the exposed orbital floor 108 region.

The snap fitted mating connectors 410a, 410b and mating receptacles 404a, 404b may include a flexible polyethylene material that enables them to deform upon forced coupling. Moreover, the first, second, and third substantially planar portions 408a, 408b, 408c may include a thickness in the region of about 0.6-1.5 millimeters and each may have an embedded titanium mesh (not shown).

It may be appreciated that the above non-limiting embodiments can be used in conjunction with any medical or other process (non-medical) involving incisions. The coupling and expanding mechanisms may also vary according to various use-parameters such as the location of the incision, size of the incision, and the surface area that the implant is required to cover. The thickness and types of materials also depend on the use (i.e., medical vs. non-medical). For example, in medical applications, the materials used in the formation of the implants should be bio-integratable and may, based on their use, have different thicknesses, flexibility, and strength.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the one or more embodiments, the practical application or technical improvement over technologies found in the marketplace, or to enable others of ordinary skill in the art to understand the embodiments disclosed herein.

What is claimed is:

1. A surgical implant device adapted for repairing injury to the floor or walls of an orbit of an eye, comprising:
    a first planar portion having a first top surface area;
    a second planar portion having a second top surface area;
    a swiveling mechanism that couples the first and the second planar portions for laterally swiveling the first and the second planar portions between an expanded state and an unexpanded state, wherein during the expanded state a first end region of the coupled first and second planar portions includes a smaller width relative to a second end region of the coupled first and second planar portions opposing the first end region; and
    an interlocking mechanism for maintaining the relative positions of the first and the second planar portions upon laterally swiveling laterally apart the first and the second planar portions to the expanded state, the interlocking mechanism including complementary interlocking structures located on the first and the second planar portions, wherein during the unexpanded state the surgical implant includes a top surface area, as observed from a plan view, corresponding to only the first top surface area of the first planar portion, and wherein during the expanded state the surgical implant includes a top surface area, as observed from a plan view, corresponding to both the first top surface area of the first planar portion and at least a portion of the second top surface area of the second planar portion,
the surgical implant being adapted for placement within an incision in the unexpanded state and adapted to be laterally swiveled to the expanded state following placement within the incision, wherein in the expanded state, the surgical implant is adapted to cover an injury surface area located within the incision that includes a width dimension that is larger relative to a width dimension of the incision, the implant device as a whole having a planar shape adapted for placement within the incision.

2. The implant device of claim 1, wherein the interlocking mechanism comprises:
    a first plurality of fins associated with the first planar portion; and
    a second plurality of fins associated with the second planar portion,
    wherein the first and the second plurality of fins are interlocked.

3. The implant device of claim 2, wherein the first and the second plurality of fins comprise a polyethylene material that enable the first and the second plurality of fins that are interlocked to forcibly move in a discrete manner with respect to each other.

4. The implant device of claim 1, wherein the first planar portion comprises a thickness of 0.6-1.5 millimeters and the second planar portion comprises a thickness of 0.6-1.5 millimeters.

5. The implant device of claim 1, wherein the first planar portion and the second planar portion comprise an embedded titanium mesh.

* * * * *